US00PP13626P29

(12) United States Plant Patent
Klemm

(10) Patent No.: US PP13,626 P2
(45) Date of Patent: Mar. 4, 2003

(54) POINSETTIA PLANT NAMED 'KLEW01064'

(75) Inventor: Nils Klemm, Stuttgart (DE)

(73) Assignee: Klemm & Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 10/036,944

(22) Filed: Dec. 31, 2001

(51) Int. Cl.[7] ..... A01H 5/00

(52) U.S. Cl. ..... Plt./307

(58) Field of Search ..... Plt./307, 306

*Primary Examiner*—Bruce R. Campell
*Assistant Examiner*—Michelle Kizilkaya
(74) *Attorney, Agent, or Firm*—C. A. Whealy

(57) ABSTRACT

A new and distinct cultivar of Poinsettia plant named 'KLEW01064', characterized by its upright and uniform plant habit; dark green-colored leaves with purple-colored petioles; bright red-colored flower bracts; very early flowering habit; and good post-production longevity.

1 Drawing Sheet

BOTANICAL CLASSIFICATION/CULTIVAR DENOMINATION

*Euphorbia pulcherrima* Willd. cultivar KLEW01064.

BACKGROUND OF THE INVENTION

The present Invention relates to a new and distinct cultivar of Poinsettia plant, botanically known as *Euphorbia pulcherrima* Willd., and hereinafter referred to by the name 'KLEW01064'.

The new Poinsettia is a product of a planned breeding program conducted by the Inventor in Stuttgart, Germany. The objective of the breeding program is to create new Poinsettia cultivars with attractive flower bract coloration and uniform plant habit.

The new Poinsettia originated from a cross made by the Inventor in 1996 of a proprietary selection of *Euphorbia pulcherrima* Willd. identified as code number K 72, not patented, as the female, or seed, parent, with a proprietary selection of *Euphorbia pulcherrima* Willd. identified as code number L52, not patented, as the male, or pollen, parent. The cultivar KLEW01064 was discovered and selected by the Inventor in 1998 as a flowering plant within the progeny of the stated cross in a controlled environment in Stuttgart, Germany. The selection of this plant was based on its attractive flower bract coloration and uniform plant habit.

Asexual reproduction of the new Poinsettia by vegetative terminal cuttings taken at Stuttgart, Germany since 1999, has shown that the unique features of this new Poinsettia are stable and reproduced true to type in successive generations of asexual reproduction.

BRIEF SUMMARY OF THE INVENTION

The following traits have been repeatedly observed and are determined to be the unique characteristics of 'KLEW01064'. These characteristics in combination distinguish 'KLEW01064' as a new and distinct Poinsettia cultivar:

1. Upright and uniform plant habit.
2. Dark green-colored leaves with purple-colored petioles.
3. Bright red-colored flower bracts.

4. Very early flowering; response time, about 6.5 weeks.
5. Good post-production longevity.

Plants of the new Poinsettia differ from plants of the female parent, the selection K 72, in the following characteristics:

1. Plants of the new Poinsettia are not as vigorous as plants of the selection K 72.
2. Leaves of plants of the new Poinsettia are more lobed than leaves of plants of the selection K 72.
3. Plants of the new Poinsettia have lighter red-colored flower bracts than plants of the selection K 72.

Plants of the new Poinsettia differ from plants of the male parent, the selection L 52, in the following chracteristics:

1. Plants of the new Poinsettia have darker green leaves than plants of the selection L 52.
2. Plants of the new Poinsettia have narrower leaves than plants of the selection L 52.

Plants of the new Poinsettia can also be compared to plants of the cultivar Fisson, disclosed in U.S. Plant Pat. No. 9,365. In side-by-side comparisions conducted in Stuttgart, Germany, plants of the new Poinsettia differed from plants of the cultivar Fisson in the following characteristics:

1. Plants of the new Poinsettia were more vigorous than plants of the cultivar Fisson.
2. Plants of the new Poinsettia flowered about one week earlier than plants of the cultivar Fisson.

BRIEF DESCRIPTION OF THE PHOTOGRAPH

The accompanying colored photograph illustrates the overall appearance of the new Poinsettia, showing the colors as true as it is reasonably possible to obtain in colored reproductions of this type. Colors in the photograph may differ slightly from the color values cited in the detailed botanical description which accurately describe the colors of the new Poinsettia. The photograph comprises a side perspective view of a single flowering plant of 'KLEW01064' grown in a container.

DETAILED BOTANICAL DESCRIPTION

Plants of the new Poinsettia have not been observed under all possible environmental conditions. The phenotype may vary somewhat with variations in environment such as temperature, daylength and light intensity, without, however, any variance in genotype.

The aforementioned photographs, following observations and measurements describe plants grown in Stuttgart, Germany under commercial practice in a glass-covered greenhouse with day temperatures ranging from 20 to 30° C. and night temperatures ranging from 16 to 20° C. Cuttings were harvested in August and planted into 12-cm containers when rooted and pinched once. Plants were flowered under natural season short day/long night conditions. Plants were about 15 weeks from unrooted cuttings when the photographs and the detailed botanical description were taken.

In the following description, color references are made to The Royal Horticultural Society Colour Chart, 1995 Edition, except where general terms of ordinary dictionary significance are used.

Botanical classification: *Euphorbia pulcherrima* Willd. cultivar KLEW01064.

Parentage:

*Female, or seed, parent.*—Proprietary selection of *Euphorbia pulcherrima* Willd. identified as code number K 72, not patented.

*Male, or pollen, parent.*—Proprietary selection of *Euphorbia pulcherrima* Willd. identified as code number L 52, not patented.

Propagation:

*Type cutting.*—Vegetative terminal cuttings.

*Time to initiate roots.*—Summer: About 12 days at 22° C. Winter: About 15 days at 22° C.

*Time to produce a rooted cutting.*—Summer: About 20 days at 22° C. Winter: About 23 days at 22° C.

*Root description.*—Fibrous and freely-branching.

Plant description:

*Growth habit.*—Upright and uniform plant habit; inverted triangle; top of plant somewhat rounded; vigorous.

*Plant height.*—About 25 to 30 cm.

*Plant diameter or spread.*—About 30 to 35 cm.

*Lateral branch description.*—Quantity per plant: About five to eight lateral branches develop after pinching. Length: About 20 cm. Diameter: About 5 to 10 mm. Internode length: About 2 to 5 cm. Texture: Smooth, glabrous. Color: 143C overlain with 183A.

*Foliage description.*—Arrangement: Alternate, single. Quantity of leaves per lateral branch: About 8 to 15. Length: About 4 to 12 cm. Width: About 2 to 7 cm. Shape: Mostly ovate with irregular lobing. Apex: Acute to acuminate. Base: Obtuse. Margin: Entire with irregular lobing. Venation pattern: Pinnate. Texture, upper and lower surfaces: Glabrous, smooth. Color: Young foliage, upper surface: 144B. Young foliage, lower surface: 143C. Fully expanded foliage, upper surface: 139A. Fully expanded foliage, lower surface: 137B. Venation, upper surface: 139A. Venation, lower surface: 138B. Petiole: Length: About 3 to 5 cm. Diameter: About 2.5 mm. Texture: Glabrous, smooth. Color, upper and lower surfaces: 183A.

Inflorescence description:

*Inflorescence type and habit.*—Inflorescences are compound corymbs of cyathia with colored flower bracts subtending the cyathia. Inflorescences not persistent.

*Fragrance.*—None detected.

*Natural flowering season.*—Autumn/winter; flower initiation and development is induced under short day/long night conditions.

*Response time.*—Very early, about 6.5 weeks.

*Post-production longevity.*—Plants of the new Poinsettia maintain good substance and bract color for about three to four weeks under interior conditions and about four to five weeks under greenhouse conditions.

*Quantity of inflorescences.*—One per lateral branch; about five to eight per plant.

*Inflorescence size.*—Diameter: About 15 to 20 cm. Height (depth): About 2 to 5 cm.

*Flower bracts.*—Quantity of fully developed flower bracts per inflorescence: About six to eight. Length: About 6 to 9 cm. Width: About 5 to 7 cm. Shape: Mostly ovate with lobing. Apex: Acute to acuminate. Base: Obtuse. Margin: Entire with lobing. Texture, upper and lower surfaces: Glabrous, smooth. Surface: Mostly flat. Color: Developing bracts, upper and lower surfaces: 45A to 45B. Fully developed bracts, upper surface: 44A; color does not fade with subsequent development. Fully developed bracts, lower surface: 47A. Venation, upper and lower surfaces: Same as flower bracts. Bract petiole: Length: About 1 to 3 cm. Diameter: About 2 mm. Texture: Glabrous, smooth. Color: 183A.

*Cyathia.*—Quantity of cyathia per corymb: About three to six. Diameter of cyathia cluster: About 1.5 to 2.5 cm. Length: About 4 to 7 mm. Diameter: About 3 to 5 mm. Shape: Ovoid. Color, immature and mature: 143C.

*Nectaries.*—Quantity of nectaries per cyanthium: One or two. Diameter: About 2 to 3 mm. Color: 13A to 14B.

*Peduncle.*—Length: About 1 to 2 mm. Diameter: About 1 mm. Aspect: Erect. Strength: Moderately strong. Texture: Glabrous, smooth. Color: 144A to 144B.

*Reproductive organs.*—Stamens: Quantity of stamens per cyathium: About 5 to 10. Anther shape: Ovoid. Anther length: About 1 mm. Anther color: 9A to 12A. Amount of pollen: Moderate. Pollen color: 9A to 12A. Pistils: Quantity of pistils per cyathium: One. Pistil length: About 3 to 5 mm. Style length: About 2 to 3 mm. Stigma color: 185A.

Disease/pest resistance: Resistance to pathogens and pests common to Poinsettias has not been observed on plants grown under commercial conditions.

It is claimed:

1. A new and distinct cultivar of Poinsettia plant named 'KLEW01064', as illustrated and described.

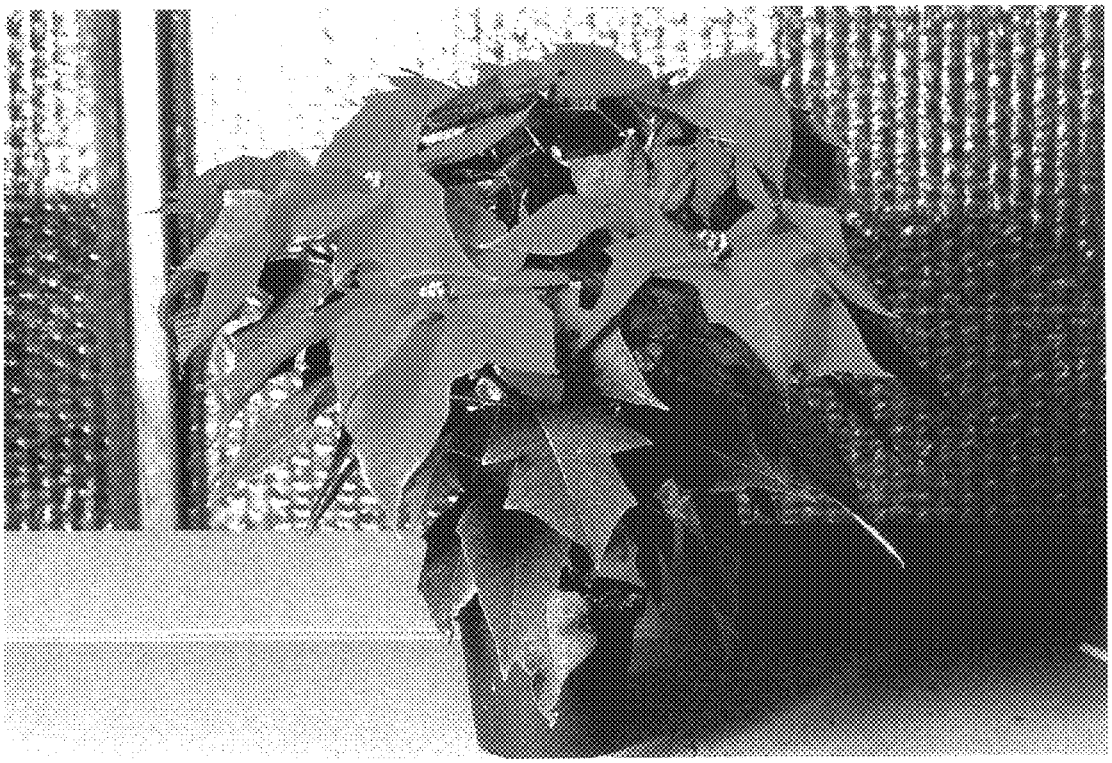

* * * * *